United States Patent [19]

Bauer et al.

[11] Patent Number: 5,508,467
[45] Date of Patent: Apr. 16, 1996

[54] PROCESS FOR THE PREPARATION OF HYDROXYALKYLAMINONITROBENZENE DERIVATIVES

[75] Inventors: Wolfgang Bauer, Maintal; Klaus Delpy, Dietzenbach; Andreas Bittner, Offenbach am Main, all of Germany

[73] Assignee: Cassella Aktiengesellschaft, Germany

[21] Appl. No.: 293,443

[22] Filed: Aug. 22, 1994

[30] Foreign Application Priority Data

Sep. 3, 1993 [DE] Germany .................... 43 29 727.7

[51] Int. Cl.$^6$ .................... C07C 209/14; C07C 269/04
[52] U.S. Cl. .................... 564/412; 564/300; 564/441; 560/22; 560/23; 560/24; 560/29; 560/30
[58] Field of Search .................... 564/300, 441, 564/412; 560/22, 23, 24, 29, 30

[56] References Cited

U.S. PATENT DOCUMENTS

| | | | |
|---|---|---|---|
| 4,125,601 | 11/1978 | Bugaut et al. | 562/22 |
| 5,091,581 | 2/1992 | Seidel | 564/412 |

Primary Examiner—Shailendra Kumar
Attorney, Agent, or Firm—Connolly & Hutz

[57] ABSTRACT

The present invention relates to a process for the preparation of compounds of the general formula I

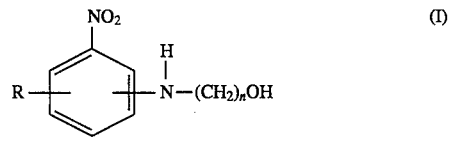

by reaction of compounds of the general formula II

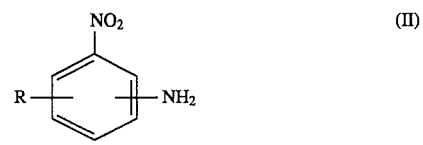

with compounds of the general formula III

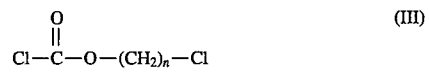

in inert aprotic solvents in the presence of a base and subsequent rearrangement of the resulting intermediate compound with an alkali metal hydroxide, characterized in that the intermediate compound is not isolated.

20 Claims, No Drawings

PROCESS FOR THE PREPARATION OF HYDROXYALKYLAMINONITROBENZENE DERIVATIVES

The present invention relates to the preparation of hydroxyalkylaminonitrobenzene derivatives by reaction of nitroaniline derivatives with chloroalkyl chloroformates and rearrangement of the resulting carbamates to give the target compounds.

Hydroxyalkylaminonitrobenzene derivatives are important intermediate products for the preparation of important dyestuffs for dyeing hair and fur.

A number of processes for their preparation have already been published, but these are all unsatisfactory either in the economic or in the ecological respect. For example, it is already known to react nitroaniline derivatives with chloroalkyl chloroformates to give the corresponding carbamates, to isolate these and if appropriate to purify them, and then to rearrange them by treatment with bases via the corresponding oxazolidinones into the target compounds (J. Am. Chem. Soc. 45, 785 (1923), Farmaco Ed. Sci. 24., 179 (1969), DE-A 38 06 237, DE-A 38 44 517, DE-A 39 17 113, DE-A 33 48 135 and DE-A 27 17 766).

The reaction to give the carbamate is usually carried out here in inert, aprotic solvents (for example benzene, acetone, dioxane, pyridine, monoethylene glycol dimethyl ether) or else without solvents in the presence of an excess of aromatic amine or of a base, such as calcium carbonate or triethylamine. Isolation and if appropriate purification by recrystallization follow.

In the processes which operate without solvent, the educts are heated to temperatures of up to 130° C., which presents problems for safety reasons. In the processes which operate with solvents, filtrates and waste waters are obtained after isolation of the product, and the solvents employed must be regenerated from these in an expensive manner, in order to avoid pollution of the environment.

According to the prior art, the carbamates prepared in this manner are rearranged with strong bases, such as sodium hydroxide or potassium hydroxide or sodium methylate, another solvent being employed, for example methanol or ethanol, and according to U.S. Pat. No. 4,910,341, even the oxazolidinone intermediate stage is also isolated.

The products prepared in this manner using alcohols usually comprise impurities in the form of aminonitrobenzene derivatives, which are formed by undesirable hydrolytic cleavage of the carbamates. Complicated and cost-intensive purification operations, for example several recrystallization operations, are therefore necessary to prepare products of high purity. Losses in yield, high pollution of the environment and thus a significant increase in the cost of the process are associated with these.

The object of the present invention is to provide a process, which is advantageous in the economic and ecological aspect, for the preparation of hydroxyalkylaminonitrobenzene derivatives.

Surprisingly, it has now been found that the carbamate intermediate stage can be reacted further without isolation, that is to say also without the use of a second solvent, a highly pure product being obtained.

The present invention thus relates to a process for the preparation of hydroxyalkylaminonitrobenzene derivatives of the general formula I

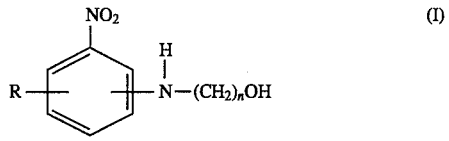

wherein
n is 2 or 3 and
R is hydrogen, hydroxyl, halogen, $(C_1-C_4)$-alkyl, $(C_1-C_4)$-alkoxy, amino, mono-$(C_1-C_4)$-alkylamino, di-$(C_1-C_4)$-alkylamino or $(C_1-C_4)$-alkylcarbonylamino,
by reaction of compounds of the general formula II

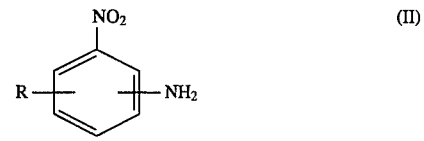

wherein
R is as defined above, with compounds of the general formula III

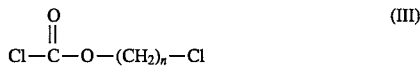

wherein
n is as defined above, in inert aprotic solvents in the presence of a base to give compounds of the general formula IV

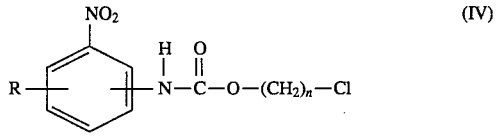

wherein
R and n are as defined above, and rearrangement of the compound of the general formula IV with an alkali metal hydroxide, characterized in that the compound of the general formula IV is not intermediately isolated.

In the general formula I, the hydroxyalkylamino group is preferably in the ortho- or meta-position relative to the nitro group.

The substituent R can occupy any of the four free positions on the benzene nucleus.

Compounds of the general formula Ia

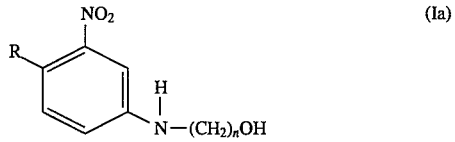

wherein n and R are as defined above, are particularly preferred.

Analogous statements apply in each case to the compounds of the general formulae II and IV. R can be $(C_1-C_4)$-alkyl which can be straight-chain or branched and is methyl, ethyl, n-propyl, i-propyl, n-butyl, i-butyl, sec.-butyl or tert.-butyl. Analogous statements apply to the alkoxy, monoalkylamino, dialkylamino and alkylcarbonylamino groups R. Halogen is, in particular, fluorine, chlorine, bromine or iodine. Preferred radicals R are hydrogen, methyl, methoxy, ethoxy, hydroxyl and chlorine.

Inert aprotic solvents to be employed according to the invention are preferably diethoxyethane, diethylene glycol dimethyl ether, triethylene glycol dimethyl ether, dioxane and tetrahydrofuran. Monoethylene glycol diethyl ether is particularly preferred, and monoethylene glycol dimethyl ether and methyl tert.-butyl ether are especially preferred.

The inert aprotic solvents can also comprise water in amounts of from 0 to 30% by weight, 1 to 10% by weight being particularly preferred.

Alkali metal carbonates, alkali metal bicarbonates, alkaline earth metal carbonates, alkaline earth metal bicarbonates, alkali metal hydroxides, alkaline earth metal hydroxides, alkaline earth metal oxides or tertiary amines can be employed as the base needed for reaction of the compounds of the general formulae II and III. Alkaline earth metal carbonates, such as calcium carbonate and magnesium carbonate, are preferred. Alkaline earth metal hydroxides, such as calcium hydroxide and magnesium hydroxide, and alkaline earth metal oxides, such as calcium oxide and magnesium oxide, are particularly preferred.

The bases mentioned are preferably employed in amounts of 0.5 to 0.7 mol, particularly preferably in amounts of 0.5 to 0.6 mol, per mol of compound of the general formula II.

The compounds of the general formula III are preferably employed in amounts of 1 to 1.4 mol, particularly preferably in amounts of 1 to 1.2 mol, per mol of compound of the general formula II.

A temperature range of 20° to 120° C. is usually maintained during the reaction of compounds of the general formulae II and III, 50° C. to 90° C. being preferred. The pH in this reaction is preferably between 3 and 10, particularly preferably between 4 and 8.

The alkali metal hydroxides needed for rearrangement of the compounds of the general formula IV are preferably lithium hydroxide, sodium hydroxide and potassium hydroxide, which can also be employed as mixtures with one another.

The alkali metal hydroxides mentioned are preferably employed in amounts of 2.5 to 4.5 mol, particularly preferably in amounts of 3.0 to 4.0 mol, and especially preferably in amounts of 3.3 to 3.7 mol, in each case per mol of compound of the general formula IV.

The alkali metal hydroxides mentioned can be employed in solid form, but preferably in the form of aqueous solutions, for example in the form of 50% strength aqueous solutions.

The rearrangement reaction is preferably carried out in a temperature range from 10° to 120° C., preferably in a temperature range from 40° to 90° C.

The process according to the invention can also be carried out in the presence of anionic, cationic or nonionic surfactants or of phase transfer catalysts.

Examples of such compounds are quaternary ammonium compounds, such as octadecyltrimethylammoniumchloride, didecyldimethylammonium chloride or trioctylmethylammonium chloride, quaternary phosphonium compounds, such as tributylhexadecylphosphonium bromide, polyethylene glycol ethers, such as pentaethylene glycol dimethyl ether or polyethylene glycol dimethyl ether of molecular weight 500, 1000 or 2000, crown ethers, such as 18-crown-6, or tris(3,6-dioxaheptyl)amine.

The compounds of the type mentioned are added in amounts of 0.01 to 5, preferably 0.1 to 2% by weight, based on the amine of the formula II employed.

The process according to the invention is carried out, for example, by a procedure in which a compound of the general formula II is dissolved in an inert aprotic solvent and reacted, as described above, with a compound of the general formula III. When the reaction has taken place water is added, if appropriate, and the salt-containing aqueous phase is separated off from the resulting two-phase mixture, in particular at pH values of 0 to 7, preferably 1 to 3. The organic phase can then be further reacted directly to give the end product. This organic phase usually has a water content of 0 to 15% by weight, preferably 1 to 10% by weight.

When the rearrangement to the compounds of the general formula I has taken place, the resulting solutions are usually separated from the alkaline salt-containing aqueous phases, if appropriate after addition of water, and are isolated by customary methods of working up, for example by redistillation of the inert solvents-employed and addition of water. Alternatively, the product can also be isolated from the two-phase mixture initially obtained, without removal of the aqueous phase. In this case, redistillation of the solvent employed is preferably carried out in a pH range of 4 to 10, particularly preferably 6 to 9.

The process according to the invention gives the compounds of the general formula I in a very high yield and in a very high purity, although neither the intermediate compounds of the general formula IV nor the end products are purified, for example by recrystallization methods. Other advantages of the process according to the invention compared with the known processes result from the fact that only one solvent is employed, instead of two. The products of the general formula I are thus accessible with a better space/time yield coupled with a significantly reduced waste water load.

In the following examples, percentage data are percentages by weight.

EXAMPLE 1

Preparation of 2-hydroxyethylamino-nitrobenzene 60.1 g of calcium carbonate are added to a solution of 138.1 g of 2-nitroaniline in 360 g of monoethylene glycol dimethylether and 60 g of water. 150.0 g of 2-chloroethyl chloroformate are then metered in at 80° C. and the reaction is brought to completion by subsequent stirring at 80° C. 100 g of water and 8.7 g of 35% strength hydrochloric acid are then added, up to a pH of 1, and the lower aqueous phase is separated off. The upper organic phase is diluted with 90 g of monoethylene glycol dimethylether, and 370.6 g of a 50% strength potassium hydroxide solution are added at 15° C. The reaction mixture is then heated to 85° C. and subsequently stirred at 85° C. for 4 hours. Thereafter, 250 g of water are added and the lower salt-containing aqueous phase is separated off. First 500 g of water and then 9 g of 10% strength sulphuric acid are added to the yellow-red organic phase, up to a pH of 8.5. After the monoethylene glycol dimethyl ether has been distilled off and the residue has been cooled to 10° C., the product is obtained in the form of yellow-red crystals.

Yield: 173.4 g
Purity: 99.8%
Yield in % of theory, based on 2-nitroaniline: 95%
2-Nitroaniline content: 0.2%
Melting point: 70°–72° C.
Comparison: Process according to DE-A 38 06 237:
Stage 1: Preparation of 2-chloroethyl 2-nitrophenylcarbamate 135 g of calcium carbonate are added to a solution of 345.3 g of 2-nitroaniline in a mixture of 1020 g of monoethylene glycol dimethyl ether and 150 g of water and the mixture is heated to 78° C. 375 g of 2-chloroethyl chloroformate are then added in the course of 3 hours. The mixture is subsequently stirred at the reflux temperature for 1.5 hours, until the reaction is complete, and is cooled to 35° C., and the product is precipitated with water and ice. The product is filtered off, washed with water and dried.

Yield: 556.5 g of pale yellow crystals
Yield in % of theory, based on 2-nitroaniline: 91%
Melting point: 64°–67° C.

Stage 2: Preparation of 2-hydroxyethylamino-nitrobenzene 244.6 g of the carbamate obtained according to Stage 1 are introduced into 900 g of water and 236 g of ethanol, the mixture is heated to 60° C. and 340.4 g of 50% strength potassium hydroxide solution are added in the course of 1.5 hours. The reaction mixture is subsequently stirred at 60° C. for 2.5 hours, brought to pH 8.0 with glacial acetic acid and allowed to cool. The product which is precipitated is filtered off with suction, washed with water, and dried at 50° C. in vacuo.

Yield: 168.8 g of yellow-red granules
Purity: 95%
Yield in % of theory, based on carbamate: 88%
Yield in % of theory, based on 2-nitroaniline: 80.1%
2-Nitroaniline content: 1.3%
Melting point: 68°–70° C.

EXAMPLE 2

4-(2-hydroxyethylamino)-2-nitroanisole

A mixture of 168.2 g of 4-amino-2-nitroanisole, 42.8 g of calcium hydroxide and 5 g of tetraethylene glycol dimethylether in 1500 g of aqueous monoethylene glycol dimethylether is reacted in accordance with the instructions of Example 1 with 150 g of 2-chloroethyl chloroformate and, after separation of the phases, with 370.6 g of 50% strength potassium hydroxide. After working up analogously to Example 1, yellow-red crystals are obtained.

Yield: 183.3 g
Purity: 99.9%
Yield in % of theory: 86.3%
4-Amino-2-nitroanisole content: 480 ppm
Melting point: 82°–84° C.

Comparison: Process according to DE-A 38 06 237:
Stage 1: 2-Chloroethyl(3-nitro-4-methoxyphenyl)carbamate 420.5 g of 4-amino-2-nitroanisole are dissolved in 1275 ml of diethylene glycol dimethyl ether and 150 ml of water, 135 g of calcium carbonate are added and the mixture is heated to 78° C. 375 g of 2-chloroethyl chloroformate are allowed to run into this mixture in the course of 3 hours such that the reaction temperature remains at 78°–80° C. The mixture is subsequently stirred for 1.5 hours to bring the reaction to completion and is cooled to 35° C. and water and ice are added. The product which has precipitated is filtered off, washed with water and dried.

Yield: 663 g
Yield in % of theory, based on 4-amino-2-nitroanisole: 96.5%
Melting point: 82°–84° C.

Stage 2: 4-hydroxyethylamino-2-nitroanisole 618 g of the carbamate obtained according to Stage 1 are initially introduced into 2025 ml of water and 675 ml of ethanol, the mixture is heated to 60° C. and 766 g of a 50% strength potassium hydroxide solution are added in the course of 1.5 hours. The mixture is subsequently stirred at 60° C. for 2.5 hours, brought to pH 8 with glacial acetic acid and cooled. The product which has precipitated is filtered off, washed with water and dried at 50° C. in vacuo.

Yield: 423.9 g of brown granules
Purity: 93.2%
Yield in % of theory, based on 4-amino-2-nitroaniline: 82.7%
4-Amino-2-nitroanisole content: 2500 ppm
Melting point: 79° C.

To obtain the product in a purity of >99% with a content of <600 ppm of 4-amino-2-nitroanisole, the product must be recrystallized several times from aqueous methanol:

1st Recrystallization 188.4 g of the product obtained according to Comparison Example 3 are dissolved in a mixture of 270 g of methanol and 590 g of water at 65° C., and 4.3 g of active charcoal are added. The mixture is then filtered and the residue is washed with a mixture of 5.5 g of methanol and 12 g of water. The filtered solution is cooled to 10° C. for crystallization. After filtration and drying, yellow-red crystals are obtained.

Yield: 162.1 g
Purity: 97.5%
Yield in % of theory, based on 4-amino-2-nitroanisole employed: 97.5%
4-Amino-2-nitroanisole content: 1100 ppm
Melting point: 80°–81° C.

2nd Recrystallization 162.1 g of the product obtained after the first recrystallization are recrystallized from a mixture of 531 g of water and 243 g of methanol with addition of 3.9 g of active charcoal. After filtration and drying, yellow-red crystals are obtained.

Yield: 142.9 g
Purity: 99.5%
Yield in % of theory, based on 4-amino-2-nitroaniline employed: 67%
4-Amino-2-nitroaniline content: 550 ppm
Melting point: 81°–83° C.

The following table shows further examples according to the invention:

| Example | Compound of the general formula II | Compound of the general formula III/n = | Base: | Solvent: | Surfactant: | Melting point of the product (°C.) |
|---|---|---|---|---|---|---|
| 3 | 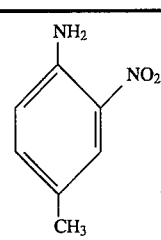 NH$_2$, NO$_2$, CH$_3$ | 2 | Ca(OH)$_2$ | Monoethylene glycol dimethyl ether | — | 77–79 |

-continued

| Example | Compound of the general formula II | Compound of the general formula III/n = | Base: | Solvent: | Surfactant: | Melting point of the product (°C.) |
|---|---|---|---|---|---|---|
| 4 | 4-Cl, 2-NO$_2$ aniline | 2 | CaCO$_3$ | Monoethylene glycol dimethyl ether | Tris-(3,6-dioxaheptyl) amine | 101–103 |
| 5 | 4-OC$_2$H$_5$, 3-NO$_2$ aniline | 2 | Ca(OH)$_2$ | Monoethylene glycol dimethyl ether | — | 74–76 |
| 6 | 4-OCH$_3$, 3-NO$_2$ aniline | 3 | Ca(OH)$_2$ | Monoethylene glycol dimethyl ether | — | red oil |
| 7 | 4-OH, 2-NO$_2$ aniline | 3 | CaCO$_3$ | Monoethylene glycol dimethyl ether | — | 115–116 |
| 8 | 4-OH, 3-NO$_2$ aniline | 2 | CaCO$_3$ | Monoethylene glycol dimethyl ether | — | 140–142 |
| 9 | 2-NO$_2$ aniline | 2 | CaCO$_3$ | Diethylene glycol dimethyl ether | Polyethylene glycol dimethyl ether MW 500 | 70–72 |
| 10 | 2-NO$_2$ aniline | 2 | MgCO$_3$ | Monoethylene glycol diethyl ether | Polyethylene glycol dimethyl ether MW 1000 | 70–72 |

-continued

| Example | Compound of the general formula II | Compound of the general formula III/n = | Base: | Solvent: | Surfactant: | Melting point of the product (°C.) |
|---|---|---|---|---|---|---|
| 11 | 2-nitroaniline | 2 | CA(OH)$_2$ | Dioxane | Polyethylene glycol dimethyl ether MW 2000 | 70–72 |
| 12 | 2-nitroaniline | 2 | CaO | Tetrahydrofuran | Pentaethylene glycol dimethyl ether | 70–72 |
| 13 | 2-nitroaniline | 2 | CaCO$_3$ | Monoethylene glycol dimethyl ether | Emulsifier MW | 70–72 |
| 14 | 2-nitroaniline | 2 | CaCO$_3$ | Monoethylene glycol dimethyl ether | Genapol X-080 | 70–72 |
| 15 | 2-nitroaniline | 2 | CaCO$_3$ | Monoethylene glycol dimethyl ether | Octadecyl tri-methylammonium chloride | 70–72 |
| 16 | 2-nitroaniline | 2 | CaCO$_3$ | Monoethylene glycol dimethyl ether | Didecyldimethyl ammonium chloride | 70–72 |
| 17 | 2-nitroaniline | 2 | CaCO$_3$ | Monoethylene glycol dimethyl ether | Trioctylmethyl ammonium chloride | 70–72 |
| 18 | 2-nitroaniline | 2 | CaCO$_3$ | Monoethylene glycol dimethyl ether | 18-Crown-6 | 70–72 |

| Example | Compound of the general formula II | Compound of the general formula III/n = | Base: | Solvent: | Surfactant: | Melting point of the product (°C.) |
|---|---|---|---|---|---|---|
| 19 | 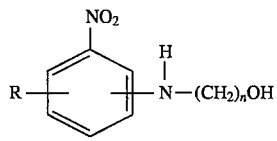 | 2 | $CaCO_3$ | Monoethylene glycol dimethyl ether | Tributyl hexadecyl phosphonium bromide | 70–72 |
| 20 | 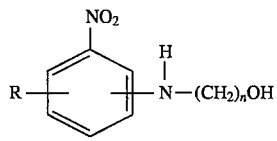 | 2 | $CaCO_3$ | Monoethylene glycol dimethyl ether | Humectol C highly concentrated | 70–72 |

Emulsifier MW is a surfactant from Bayer AG
Genapol X-080 is a surfactant from Hoechst AG
Humectol C is a surfactant from Hoechst AG

We claim:

1. Process for the preparation of hydroxyalkylaminonitrobenzene derivatives of formula I

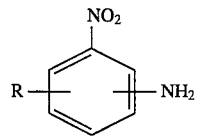

wherein n is 2 or 3 and

R is hydrogen, hydroxyl, halogen $(C_1-C_4)$-alkyl, $(C_1-C_4)$-alkoxy, amino, mono-$(C_1-C_4)$-alkylamino, di-$(C_1-C_4)$-alkylamino or $(C_1-C_4)$-alkylcarbonylamino, comprising reacting compounds of formula II

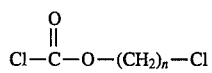

wherein

R is as defined above, with compounds of formula III $$Cl-\overset{O}{\overset{\|}{C}}-O-(CH_2)_n-Cl \qquad (III)$$

wherein n is as defined above, in inert aprotic solvents in the presence of a base to give compounds of formula IV

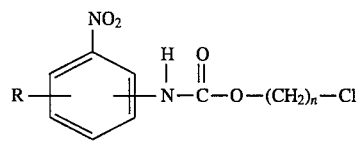

wherein

R and n are as defined above, and rearrangement of the compound of formula IV with an alkali metal hydroxide, wherein compound of the formula IV is not intermediately isolated, and wherein, when the reaction of the compound of the formula II with the compound of the formula III has taken place, water is added to the reaction mixture, optionally, and the salt containing aqueous phase is separated off from the resulting two-phase mixture at pH values of 0 to 7, and the organic phase is further reacted to give the end product of formula I.

2. The process according to claim 1, wherein R is in the ortho- or meta-position relative to the nitro group.

3. The process according to claim 1, wherein the compound of formula (I) is a compound of formula Ia

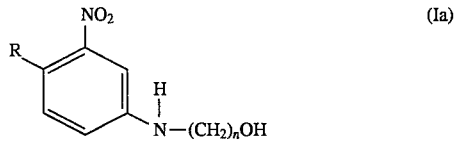

wherein R and n are as defined in claim 1.

4. The process according to claim 1, wherein R is hydrogen, methyl, methoxy, ethoxy, hydroxyl or chlorine.

5. The process according to claim 3, wherein R is hydrogen, methyl, methoxy, ethoxy, hydroxyl or chlorine.

6. The process according to claim 1, wherein the inert aprotic solvents are selected from the group consisting of diethoxyethane, diethylene glycol dimethyl ether, triethylene glycol dimethyl ether, dioxane, tetrahydrofuran, monoethylene glycol diethyl ether, monoethylene glycol dimethyl ether and methyl tert.-butyl ether.

7. The process according to claim 5, wherein the inert aprotic solvents are monoethylene glycol dimethyl ether, methyl tert.-butyl ether or monoethylene glycol diethyl ether.

8. The process according to claim 1, wherein the inert aprotic solvents contain an effective amount of water up to about 30% by weight of water.

9. The process according to claim 7, wherein the inert aprotic solvents contain from about 1 to about 10% by weight of water.

10. The process according to claim 1, wherein the base is alkali metal carbonates, alkali metal bicarbonates, alkaline earth metal carbonates, alkaline earth metal bicarbonates, alkali metal hydroxides, alkaline earth metal hydroxides, alkaline earth metal oxides of tertiary amines or mixtures thereof.

11. The process according to claim 9, wherein the base is calcium carbonate, magnesium carbonate, calcium hydroxide, magnesium hydroxide, calcium oxide, magnesium oxide, lithium hydroxide, sodium hydroxide or potassium hydroxide or mixtures thereof.

12. The process according to claim 10, wherein the alkali metal hydroxide is lithium hydroxide, sodium hydroxide or potassium hydroxide or mixtures thereof.

13. The process according to claim 11, wherein the alkali metal hydroxide is lithium hydroxide, sodium hydroxide or potassium hydroxide or mixtures thereof.

14. The process according to claim 1, wherein the base is present in an amount from about 0.5 to about 0.7 mol per mol of compound of formula II.

15. The process according to claim 13, wherein the base is present in an amount from about 0.5 to about 0.6 mol per mol of compound of formula II.

16. The process according to claim 1, wherein the reaction of formula II and formula III is carried out in a temperature range from about 20° to about 120° C. and the pH is from about 3 to about 10.

17. The process according to claim 15, wherein the reaction of formula II and formula III is carried out in a temperature range from about 50° to about 90° C. and the pH is from about 4 to about 8.

18. The process according to claim 1, wherein the compounds of formula III are present in an amount from about 1 to about 1.4 mol per mol of compound of formula II and the alkali metal hydroxide used in the rearrangement is in an amount from about 2.5 to about 4.5 mol per mol of compound of formula IV.

19. The process as claimed in claim 17, wherein the compound of formula III is present in an amount from about 1 to about 1.2 mol per mol of compound of formula II and the alkali metal hydroxide is selected from the group consisting of lithium hydroxide, sodium hydroxide, potassium hydroxide and a mixture thereof in an amount from about 3.3 to about 3.7 mol per mol of compound of formula IV.

20. Process according to claim 1, wherein the reaction is carried out in the presence of anionic, cationic or nonionic surfactants or of phase transfer catalysts.

* * * * *